United States Patent
Wu et al.

(10) Patent No.: US 10,962,519 B2
(45) Date of Patent: Mar. 30, 2021

(54) ANALYSIS PRETREATMENT DEVICE

(71) Applicant: TOSHIBA MEMORY CORPORATION, Tokyo (JP)

(72) Inventors: Jiahong Wu, Mie (JP); Ayako Mizuno, Mie (JP); Yuji Yamada, Mie (JP)

(73) Assignee: TOSHIBA MEMORY CORPORATION, Tokyo (JP)

( * ) Notice: Subject to any disclaimer, the term of this patent is extended or adjusted under 35 U.S.C. 154(b) by 644 days.

(21) Appl. No.: 15/066,271

(22) Filed: Mar. 10, 2016

(65) Prior Publication Data

US 2017/0072378 A1 Mar. 16, 2017

(30) Foreign Application Priority Data

Sep. 11, 2015 (JP) .............................. JP2015-179739

(51) Int. Cl.
| | |
|---|---|
| *B01J 19/24* | (2006.01) |
| *G01N 1/40* | (2006.01) |
| *G01N 1/44* | (2006.01) |
| *G01N 23/207* | (2018.01) |
| *G01N 33/20* | (2019.01) |
| *G01N 35/00* | (2006.01) |
| *G01N 33/00* | (2006.01) |

(52) U.S. Cl.
CPC ............ *G01N 33/20* (2013.01); *G01N 1/4044* (2013.01); *G01N 1/44* (2013.01); *G01N 2033/0095* (2013.01)

(58) Field of Classification Search
None
See application file for complete search history.

(56) References Cited

U.S. PATENT DOCUMENTS

| | | | | |
|---|---|---|---|---|
| 3,604,698 A | * | 9/1971 | Themelis | .................. C22B 9/05 266/226 |
| 4,749,440 A | | 6/1988 | Blackwood et al. | |
| 5,777,300 A | * | 7/1998 | Homma | ............ H01L 21/67115 118/715 |
| 6,053,984 A | * | 4/2000 | Petvai | ...................... G01N 1/32 134/2 |
| 6,077,451 A | | 6/2000 | Takenaka et al. | |
| 8,932,954 B2 | | 1/2015 | Yamada et al. | |

(Continued)

FOREIGN PATENT DOCUMENTS

| | | |
|---|---|---|
| JP | S62-502930 A | 11/1987 |
| JP | 5-90378 | 4/1996 |

(Continued)

*Primary Examiner* — Kathryn Wright
(74) *Attorney, Agent, or Firm* — Finnegan, Henderson, Farabow, Garrett & Dunner L.L.P.

(57) ABSTRACT

An analysis pretreatment device according to an embodiment includes a chamber capable of containing an analysis object therein. A pressure reducer reduces pressure inside the chamber. An introducing part vaporizes a liquid and introduces the vaporized liquid into the chamber. A first supplier supplies water in a liquid state to the introducing part. A second supplier supplies hydrofluoric acid in a gas state to the introducing part. The introducing part introduces a mixed gas into the chamber. The mixed gas includes vaporized water, which is obtained by vaporizing water in a liquid state, and hydrofluoric acid in a gas state.

13 Claims, 5 Drawing Sheets

(56) References Cited

U.S. PATENT DOCUMENTS

| | | | |
|---|---|---|---|
| 2003/0043963 A1* | 3/2003 | Yamagami | G01N 23/223 |
| | | | 378/44 |
| 2005/0196881 A1* | 9/2005 | Shiramizu | G01N 1/4044 |
| | | | 438/14 |
| 2005/0208674 A1 | 9/2005 | Tokushima et al. | |
| 2012/0149199 A1* | 6/2012 | Yamada | G01N 1/2813 |
| | | | 438/694 |

FOREIGN PATENT DOCUMENTS

| JP | 2001-196432 | 7/2001 |
|---|---|---|
| JP | 2005-3422 A | 1/2005 |
| JP | 2013-190403 A | 9/2013 |
| JP | 2015-38452 | 2/2015 |

\* cited by examiner

ANALYSIS PRETREATMENT DEVICE

CROSS REFERENCE TO RELATED APPLICATIONS

This application is based upon and claims the benefit of priority from the prior Japanese Patent Application No. 2015-179739, filed on Sep. 11, 2015, the entire contents of which are incorporated herein by reference.

FIELD

The embodiments of the present invention relate to an analysis pretreatment device.

BACKGROUND

Metal impurities present in a semiconductor thin film deteriorate an oxide film breakdown voltage or lead to crystal defects, resulting in deterioration of characteristics of a semiconductor device. Therefore, analysis of metal impurities present in a semiconductor thin film is performed.

In a case where an object of examination is a natural oxide film or a thermal oxide film on a semiconductor substrate, the oxide film is decomposed by vapor phase decomposition using hydrofluoric acid. Silicate generated by the vapor phase decomposition is reduced by being vaporized by heat treatment or the like. Thereafter, the substrate is scanned with a chemical liquid such as hydrofluoric acid-hydrogen peroxide mixture, and the chemical liquid is then collected.

In this manner, metal impurities on the substrate are taken into the chemical liquid and are collected. This chemical liquid is then analyzed by a total refection X-ray fluorescence (hereinafter, "TXRF") method, for example.

However, in a case where an object of examination is a nitride film or an oxynitride film, decomposition takes a long time and a particle diameter of ammonium fluorosilicate $((NH_4)_2SiF_4)$ generated by a reaction between hydrofluoric acid and the nitride film or the oxynitride film becomes large according to a conventional vapor phase decomposition method. Water droplets (a decomposition liquid) are condensed on the substrate that is hydrophobic by using this ammonium fluorosilicate as nuclei. As the decomposition time is longer, the water droplets (the decomposition liquid) are larger and it takes a considerably long time to decompose the ammonium fluorosilicate by heat treatment. Further, long-time decomposition causes a back surface of the semiconductor substrate to be exposed with hydrofluoric acid and be decomposed, so that resultant ammonium fluorosilicate contaminates a stage or the like. Therefore, a nitride film or an oxynitride film is not suitable for an automated collecting apparatus that automatically performs operations from vapor phase decomposition to collection or analysis.

DETAILED DESCRIPTION

An analysis pretreatment device according to an embodiment includes a chamber capable of containing an analysis object therein. A pressure reducer reduces pressure inside the chamber. An introducing part vaporizes a liquid and introduces the vaporized liquid into the chamber. A first supplier supplies water in a liquid state to the introducing part. A second supplier supplies hydrofluoric acid in a gas state to the introducing part. The introducing part introduces a mixed gas into the chamber. The mixed gas includes vaporized water, which is obtained by vaporizing water in a liquid state, and hydrofluoric acid in a gas state.

Embodiments will now be explained with reference to the accompanying drawings. The present invention is not limited to the embodiments.

Figure 1:
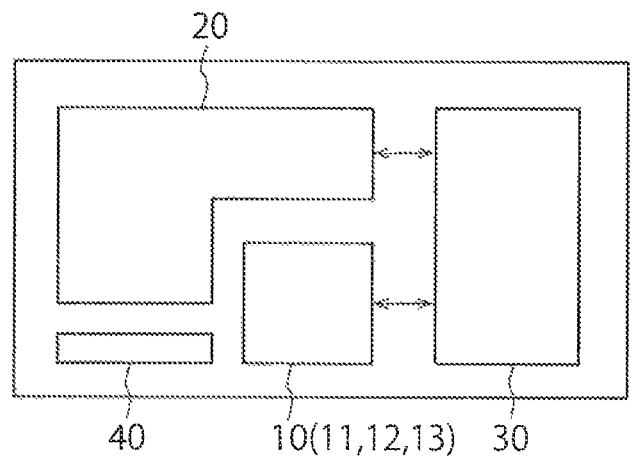
FIG. 1 is a plan view of an impurity analyzer 1 according to an embodiment.
Figure 2:
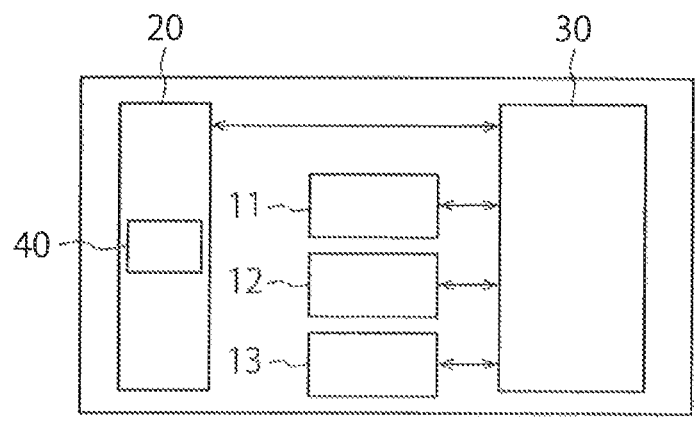
FIG. 2 is a front view of the impurity analyzer 1.

FIG. 1 is a plan view (a transverse cross-sectional view) of an impurity analyzer 1 according to an embodiment, and FIG. 2 is a front view (a longitudinal cross-sectional view) of the impurity analyzer 1. The impurity analyzer 1 is an apparatus that analyzes metal impurities included in a material film as an object of analysis formed on a substrate by vapor phase decomposition (VPD). As shown in FIGS. 1 and 2, the impurity analyzer 1 includes a pretreatment device 10, an X-ray fluorescence analyzer 20, a transporting device 30, and a controller 40. The impurity analyzer 1 is an automated analyzing apparatus that automatically performs operations from vapor phase decomposition to analysis.

Although the metal impurities are analyzed by a TXRF method in the present embodiment, an inductively coupled plasma mass spectrometry (hereinafter, "ICP-MS") method or an atomic absorption spectrometry (hereinafter, "AAS") method can be used, for example.

The pretreatment device 10 as an analysis pretreatment device includes a vapor-phase decomposing part 11, a heater 12, and a sample collector 13. The pretreatment device 10 can be incorporated in the impurity analyzer 1 or can be provided separately from other components of the impurity analyzer 1.

The X-ray fluorescence analyzer 20 (hereinafter, simply "analyzer") 20 radiates an X-ray and analyzes an object to be measured on a substrate. For example, the analyzer 20 can be a total reflection X-ray fluorescence (TXRF) analyzer that makes an X-ray incident on a surface of the substrate at a very low angle and analyzes metal contamination of the surface of the substrate by using total reflection of the X-ray from the surface of the substrate. The analyzer 20 can be any device, so long as it can perform metal analysis. For example, the analyzer 20 can be an ICP-MS device or an AAS device, for example.

The transporting device 30 has a robot hand (see 32 in FIGS. 3 and 4), for example, and can transport the substrate between the vapor-phase decomposing part 11, the heater 12, the sample collector 13, and the analyzer 20. The controller 40 controls each of the components of the impurity analyzer 1.

The vapor-phase decomposing part 11 of the pretreatment device 10 dissolves a material film on the surface of the substrate and metal impurities present in the material film by using a process gas, and holds the metal impurities and the material film that have been dissolved on the surface of the substrate. A more detailed configuration of the vapor-phase decomposing part 11 will be described later with reference to FIG. 3.

The heater 12 of the pretreatment device 10 heats and dries the substrate. For example, the heater 12 includes a chamber made of PTFE. The transporting device 30 transports the substrate into or out from the chamber of the heater 12. A hot plate is provided in the chamber of the heater 12. The substrate is heated while being placed on the hot plate. The hot plate is larger than the substrate. The temperature of heating by the hot plate is controlled by the controller 40.

The sample collector 13 of the pretreatment device 10 supplies a collecting liquid onto the surface of the substrate from a nozzle thereof, and moves the collecting liquid to the center of the substrate with the nozzle while holding and rotating the substrate by a rotary holding part. Accordingly, the sample collector 13 collects an object to be measured (metal impurities) present on the surface of the substrate into the collecting liquid. In a case of a TXRF analyzer, a heating part, such as a lamp, is provided within the sample collector 13, so that the collecting liquid into which the object to be measured has been collected is heated and the object to be measured is dried. A more detailed configuration of the sample collector 13 will be described later with reference to FIG. 4.

Figure 3:
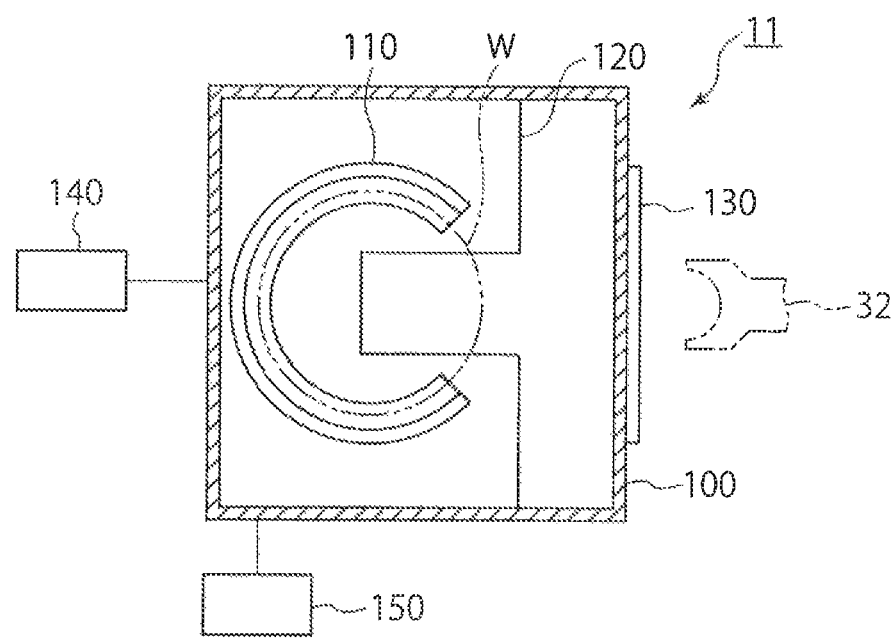
FIG. 3 is a plan view showing a configuration example of the vapor-phase decomposing part 11.

FIG. 3 is a plan view showing a configuration example of the vapor-phase decomposing part 11. The vapor-phase decomposing part 11 performs vapor phase decomposition of a material film on a substrate W by using a process gas. The vapor-phase decomposing part 11 includes a chamber 100, a stage 110, a section plate 120, a transport inlet 130, a process-gas supplying part 140, and a vacuum pump 150.

The chamber 100 can contain the substrate W transported through the transport inlet 130. PTFE (polytetrafluoroethylene) is used for the chamber 100, for example. The pressure inside the chamber 100 is reduced by the vacuum pump 150 as a pressure-reducer. The substrate W has a material film (not shown) as an object of analysis on a surface thereof.

The stage 110 is provided in the chamber 100 in such a manner that the substrate W can be placed thereon. The stage 110 is fixed inside the chamber 100 via the section plate 120 protruding horizontally from a sidewall of the chamber 100. The section plate 120 has a notch that prevents interference of the robot arm 32 of the transporting device 30 with the section plate 120. With this configuration, the transporting device 30 can transport the substrate W into the chamber 100 through the transport inlet 130 to place the substrate W on the stage 110 and can transport the substrate W from the stage 110 to the outside of the chamber 100.

The process-gas supplier 140 introduces a process gas that decomposes the material film (for example, an oxide film, a nitride film, or an oxynitride film) on the substrate W into the chamber 100. The process gas is a gas for dissolving the material film, and is fluorine-containing gas in which hydrofluoric acid in a gas state and water in a liquid state are mixed, for example. A cleaning-liquid supply pipe for supplying a cleaning-liquid (for example, pure water) for cleaning the surface of the substrate W, an inert-gas supply pipe for supplying an inert gas (for example, nitrogen gas) into the chamber 100, and an exhaust pipe (not shown) for discharging a gas inside the chamber 100 may be provided other than the process-gas supplier 140. Accordingly, the vapor-phase decomposing part 11 can introduce an inert gas such as nitrogen gas and can purge the process gas.

Figure 4:
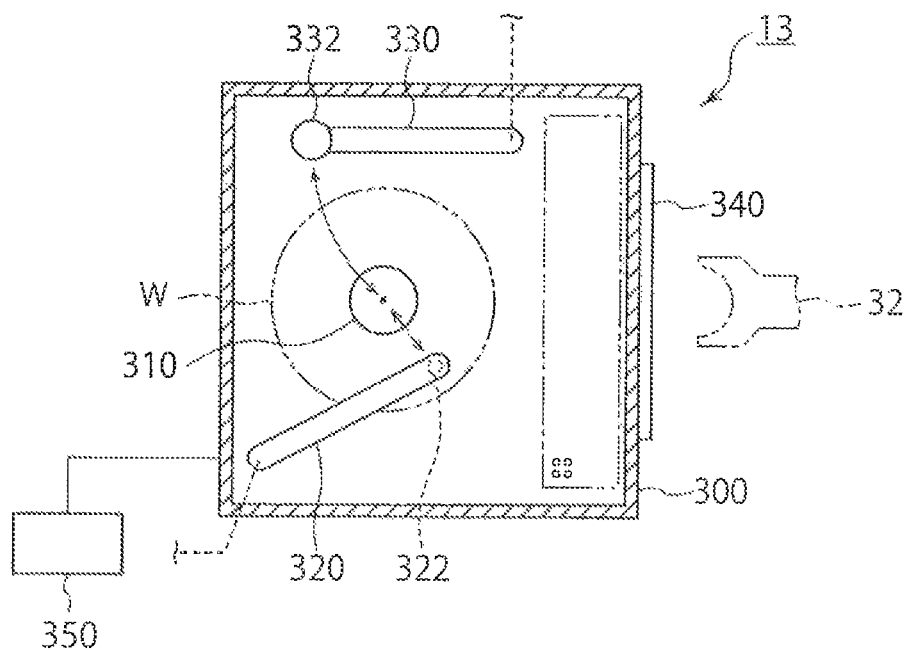
FIG. 4 is a plan view showing a configuration example of the sample collector 13.

FIG. 4 is a plan view showing a configuration example of the sample collector 13. The sample collector t 13 collects an object to be measured (metal impurities) that remains after vapor phase decomposition of a material film in the vapor-phase decomposing part 11, in order to analyze the object to be measured. The sample collector 13 includes a chamber 300, a stage 310, a collecting-liquid moving part 320, a collecting-liquid drier 330, a transport inlet 340, and a vacuum pump 350. Although the collecting-liquid drier 330 is provided in a TXRF analyzer, it is not necessarily provided in an ICP-MS device or an atomic absorption spectrometry device.

The chamber 300 can contain the substrate W transported through the transport inlet 340. PTFE is used for the chamber 300, for example. The pressure inside the chamber 300 is reduced by the vacuum pump 350. The robot arm 32 transports the substrate W from the heater 12 to the sample collector 13 after heat treatment, and transports the substrate W into the chamber 300 through the transport inlet 340.

The stage 310 is provided inside the chamber 300 in such a manner that the substrate W can be placed thereon. The stage 310 can be rotated while holding the substrate W substantially horizontally.

A nozzle 322 is provided at one end of the collecting-liquid moving part 320. The other end of the collecting-liquid moving part 320 is connected to an axis and is configured to be rotatable around the axis. The collecting-liquid moving part 320 rotates around the axis to be able to move the nozzle 322 substantially horizontally between an end portion and a center portion of the substrate W. The nozzle 322 supplies a collecting liquid to the surface of the substrate W and holds the collecting liquid. The surface of the substrate W is lyophobic. Therefore, the collecting liquid does not flow from immediately below the nozzle 322, but can be held between the nozzle 322 and the substrate W. The collecting-liquid moving part 320 supplies the collecting liquid to the surface of the substrate W, and moves the collecting liquid from the end portion to the center portion of the substrate W while rotating the substrate W. Accordingly, the entire surface of the substrate W can be scanned with the collecting liquid, so that the object to be measured (the metal impurities) present on the surface of the substrate W can be collected to the center of the substrate W. The collecting liquid may be a mixed aqueous solution of about 2% hydrofluoric acid and about 2% hydrogen peroxide solution, or a mixed aqueous solution of about 1% hydrofluoric acid and about 3% hydrogen peroxide solution, for example. Further, the collecting liquid may be a mixed aqueous solution of hydrofluoric acid, hydrochloric acid, and water, a mixed aqueous solution of hydrochloric acid and hydrogen peroxide solution, or a mixed aqueous solution of nitric acid, hydrochloric acid, and hydrofluoric acid, for example.

A lamp 332 that irradiates light on the collecting liquid on the substrate W to heat the collecting liquid is provided at one end of the collecting-liquid drier 330. The other end of the collecting-liquid drier 330 is connected to an axis. The collecting-liquid drier 330 is configured to be rotatable around the axis. The collecting-liquid drier 330 rotates around the axis to be able to move the lamp 332 substantially horizontally between the end portion and the center portion of the substrate W. The lamp 332 is an infrared lamp, for example. With this configuration, the collecting-liquid drier 330 heats the collecting liquid into which the object to be measured has been collected by the lamp 332, to dry the object to be measured. The collecting-liquid drier 330 can dry the collecting liquid by a heating part other than the lamp.

Because the above description is made on the sample collector 13 in a case of analysis by a TXRF method, the collecting-liquid drier 330 dries the collecting liquid at the center portion of the substrate W. However, in a case of analysis by an ICP-MS method or an AAS method, the collecting-liquid drier 330 is unnecessary and the collecting liquid is transported in a liquid form to an analyzer (not shown) of the ICP-MS method or the AAS method.

Figure 5:
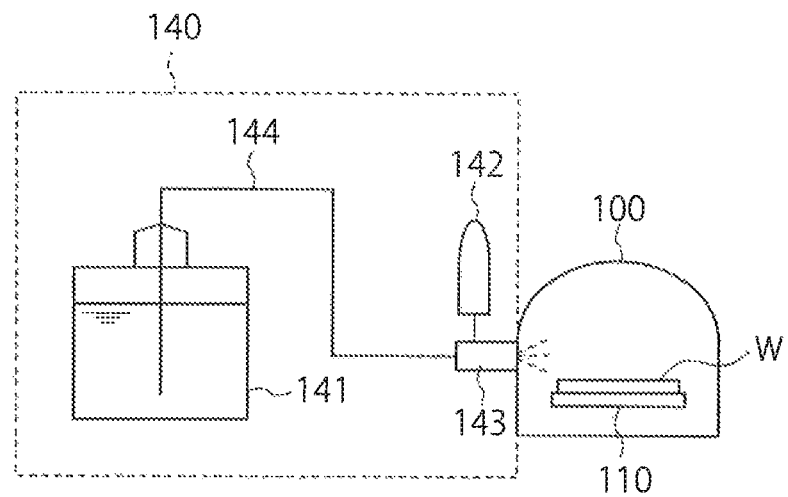
FIG. 5 shows a configuration example of the chamber 100 and the process-gas supplying part 140 in the pretreatment device 10.

FIG. 5 shows a configuration example of the chamber 100 and the process-gas supplier 140 in the pretreatment device 10. As described above, the chamber 100 is configured to be able to contain the substrate W therein. The substrate W is placed on the stage 110. The pressure inside the chamber 100 is reduced by the vacuum pump 150 shown in FIG. 3.

The process-gas supplier 140 includes a first supplier 141, a second supplier 142, an Introducing part 143, and a pipe 144.

The first supplier 141 contain s therein water in a liquid state and supplies the water in a liquid state to the introducing part 143 via the pipe 144. The first supplier 141 is a tank containing therein water in a liquid state, for example. The pipe 144 connects between the first supplier 141 and the introducing part 143 and transports water in a liquid state to the introducing part 143.

The second supplier 142 contains hydrofluoric acid therein and supplies hydrofluoric acid in a gas state to the Introducing part 143. The second supplier 142 can be a hydrofluoric-acid gas cylinder that contain s therein the hydrofluoric acid in a gas state that is compressed, for example. In this case, because the hydrofluoric acid is compressed, it may be contained in a liquid state in the second supplier 142. When the hydrofluoric acid is supplied from the second supplier 142 to the introducing part 143, hydrofluoric acid is supplied in a gas state. Further, the concentration (purity) of the hydrofluoric acid contained in the second supplier 142 is very high, being at least 99% or more, and is preferably approximately 100%.

The introducing part 143 sprays the water from the first supplier 141 to vaporize the water. Further, the introducing part 143 mixes the hydrofluoric acid in a gas state from the second supplier 142 into the vaporized water and introduces the mixture into the chamber 100. For example, the Introducing part 143 is a sprayer, such as a nebulizer, and vaporizes the water by using the hydrofluoric acid gas as a carrier and introduces the mixture into the chamber 100.

Figure 6:
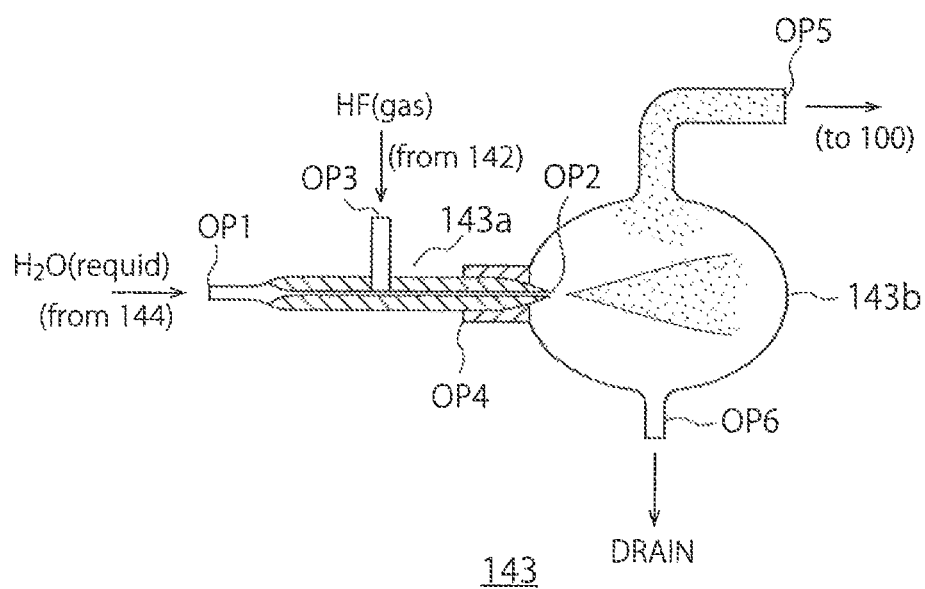
FIG. 6 shows a configuration example of the introducing part 143.

FIG. 6 shows a configuration example of the introducing part 143. The introducing part 143 includes a spraying part 143*a* and a gas-liquid separator 143*b*.

A liquid-supply opening OP1 is provided at one end of the spray 143*a*. The liquid-supply opening OP1 is connected to the pipe 144 and receives water in a liquid state. A spray opening OP2 is provided at the other end of the spray 143*a*. The spray opening OP2 is connected to the gas-liquid separator 143*b* and sprays a liquid or a gas in a mist form to the gas-liquid separator 143*b*. A gas-supply opening OP3 is provided between the liquid-supply opening OP1 and the spray opening OP2 of the spray 143*a*. The gas-supply opening OP3 is connected to the second supplier 142 and receives the hydrofluoric acid gas.

The spray 143*a* has an inner diameter decreasing from one end (the liquid-supply opening OP1) to the other end (the spray opening OP2), and sprays a liquid or a gas in a mist form from the spray opening OP2 by a pressure applied from the liquid-supply opening OP1 of the spray 143*a*. In the present embodiment, the spray 143*a* mixes the hydrofluoric acid in a gas state into the water, when spraying the water in a liquid form to vaporize the water.

An opening OP4 at one end of the gas-liquid separator 143*b* is connected to the spray opening OP2 of the spray 143*a* and receives the water in a liquid form and a gas form and the hydrofluoric acid in a gas form that are sprayed from the spray 143*a*. A gas-supply opening OP5 is provided at an upper portion of the gas-liquid separator 143*b*. The gas-supply opening OP5 is connected to the chamber 100 and introduces a mixed gas of the vaporized water and the hydrofluoric acid in a gas state into the chamber 100. A liquid-discharge opening OP6 is provided as a drain at a lower portion of the gas-liquid separator 143*b*. The liquid-discharge opening OP6 discharges the water, remaining in a liquid form that has not been vaporized, to the outside of the gas-liquid separator 143*b*. The water in a liquid state can be discharged from the liquid-discharge opening OP6 by falling downwards by gravity or forcedly by a liquid-discharge pump. In this manner, the gas-liquid separator 143*b* can separate the mixed gas of the vaporized water and the hydrofluoric acid in a gas state from the water in a liquid form, introduce the mixed gas into the chamber 100, and discharge the water in a liquid form.

Next, a process of vapor phase decomposition according to the present embodiment is described.

Figure 7:
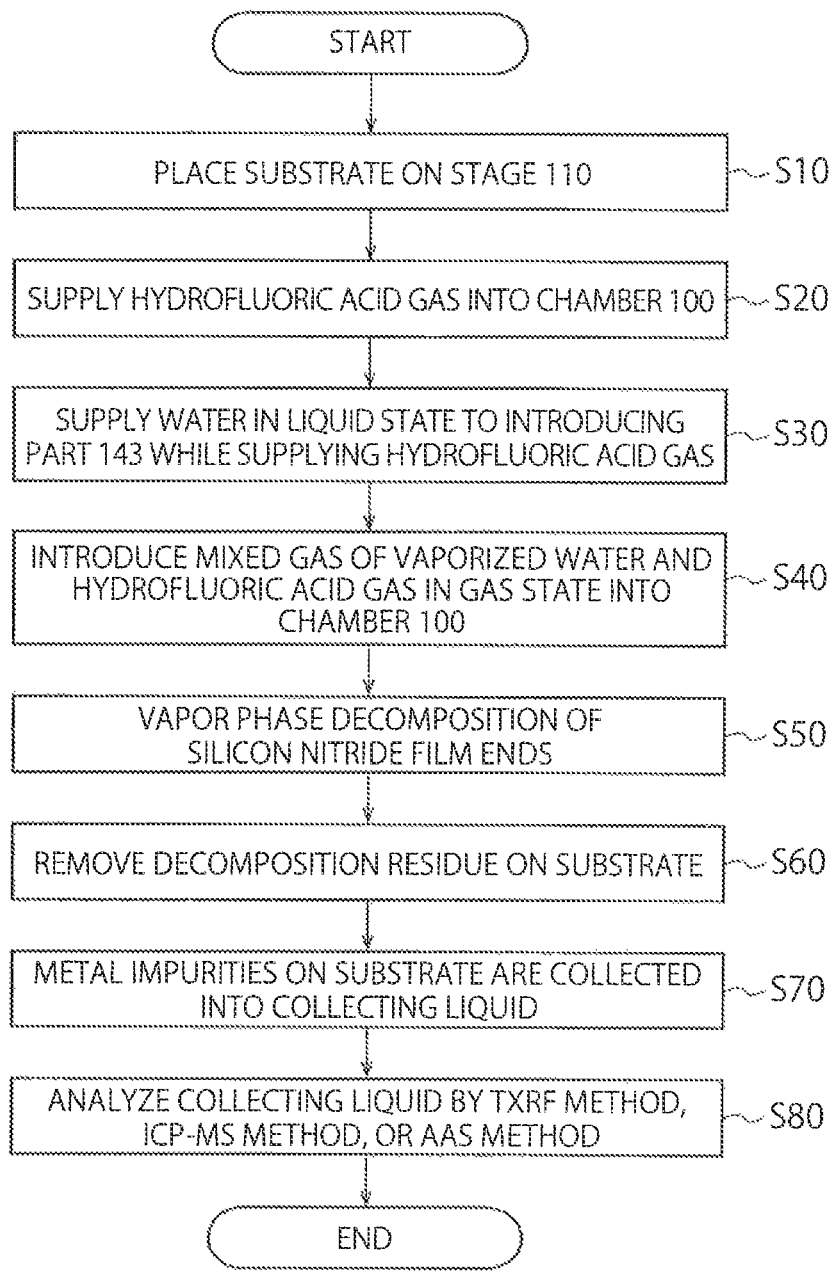
FIG. 7 is a flowchart showing an example of steps of vapor phase decomposition using the pretreatment device 10.

FIG. 7 is a flowchart showing an example of steps of vapor phase decomposition using the pretreatment device 10. In the present embodiment, an object of analysis is a silicon nitride film formed on a semiconductor substrate, for example. The silicon nitride film has a film thickness of about 200 nm, for example. The pretreatment device 10 performs vapor phase decomposition of the silicon nitride film as pretreatment, in order to analyze metal impurities included in a nitride film or an oxynitride film.

First, a substrate is placed on the stage 110 (S10).

Subsequently, the second supplier 142 supplies a hydrofluoric acid gas into the chamber 100 at a flow rate of about 1 l/min for about 5 minutes, for example (S20). Accordingly, the inside of the chamber 100 is filled with the hydrofluoric acid gas. At this time, the first supplier 141 does not supply water to the chamber 100. Therefore, almost no vapor phase decomposition of the silicon nitride film occurs, because the chamber 100 has almost no water content therein although the chamber 100 is filled with the hydrofluoric acid gas.

The first supplier 141 then supplies water in a liquid state to the introducing part 143 at a flow rate of about 5 to 50 μl/min, for example, while the flow rate of the hydrofluoric acid gas at Step S20 is maintained (S30). Thus, the Introducing part 143 starts to spray the water and introduces a mixed gas of the vaporized water and the hydrofluoric acid gas in a gas state into the chamber 100 (S40). The start of introduction of the mixed gas causes vapor phase decomposition of the silicon nitride film to be started. The introduction of the mixed gas is performed for about 5 to 15 minutes, for example, with which vapor phase decomposition of the silicon nitride film is ended (S50). In the present embodiment, vapor phase decomposition of the silicon nitride film is performed by using the mixed gas of the vaporized water and the hydrofluoric acid gas in a gas state. In this case, the water content improves wettability on the silicon nitride film, and the hydrofluoric acid gas can come into contact with the silicon nitride film more easily. Therefore, an etching rate of the silicon nitride film by the hydrofluoric acid gas is increased, and vapor phase decomposition of the silicon nitride film can be performed in a relatively short period of time.

After vapor phase decomposition of the silicon nitride film, nitrogen gas is supplied into the chamber 100 for about 10 minutes to purge the gas inside the chamber 100. Silicon compounds of large amount are deposited on the substrate by vapor phase decomposition of the nitride film.

The substrate is then transported to the heater 12 and is placed on the hot plate. The substrate is heated on the hot plate heated to about 110° C. for about 10 minutes. This heating dries solution droplets (a decomposed silicon nitride film) on the substrate.

Subsequently, the temperature of the hot plate is raised to about 230° C., and the substrate is further heated for about 5 minutes. Accordingly, a decomposition residue (a silicon compound deposited at Step S50 or ammonium fluorosilicate (($NH_4$)$_2$$SiF_4$)) on the substrate is removed (S60). Ammonium fluorosilicate forms larger particles as a process time of vapor phase decomposition of the silicon nitride film is longer. Therefore, in a case where the process time of vapor phase decomposition is short and the particles of ammonium fluorosilicate are small, the ammonium fluorosilicate can be removed by heat treatment, similarly to other silicon compounds.

After the substrate is lifted from the hot plate with lift pins or the like and is cooled, the substrate is transported to the sample collector 13 and is held by the rotary holding part. About 0.1 ml of a collecting liquid is dropped on the substrate, scanning with the collecting liquid is performed for the entire surface of the substrate, and metal impurities on the substrate are collected into the collecting liquid (S70). For example, a mixed solution containing about 2% of hydrofluoric acid and about 2% of hydrogen peroxide solution is used as the collecting liquid. In a case of collecting metal impurities of which a collecting efficiency is low when the mixed solution of hydrofluoric acid and the hydrogen peroxide solution is used, a mixed aqueous solution of hydrofluoric acid, hydrochloric acid, and water, a mixed solution of hydrochloric acid and hydrogen peroxide solution, or a mixed aqueous solution of nitric acid, hydrochloric acid, and hydrofluoric acid can be used as the collecting liquid.

The collecting liquid in which the metal impurities are dissolved is then dried and analyzed by a TXRF method (S80). Alternatively, the collecting liquid is analyzed by an ICP-MS method or an AAS method as it is without being dried. By this analysis, the type, the content, and the like of the metal impurities included in the silicon nitride film are identified.

When spraying the water in a liquid state to vaporize the water, the pretreatment device 10 according to the present embodiment mixes the hydrofluoric acid in a gas state into the water and introduces the mixture gas of the vaporized water and the hydrofluoric acid in a gas state into the chamber 100. The hydrofluoric acid gas supplied here has a very high concentration, and has a concentration of 99% or more (approximately 100%). Therefore, it is possible to introduce the hydrofluoric acid having a high concentration together with the vaporized water into the chamber 100. The water content improves wettability on the silicon nitride film, and the hydrofluoric acid gas can come into contact with the silicon nitride film more easily. In this manner, the etching rate of the silicon nitride film by the hydrofluoric acid gas is increased and the time of vapor phase decomposition of a silicon nitride film or a silicon oxynitride film is reduced. The reduction of the time of vapor phase decomposition leads to reduction of the time of entire metal analysis. Further, as the time of vapor phase decomposition is shorter, particles of the decomposition residue (for example, ammonium fluorosilicate) remaining on the substrate after vapor phase decomposition are smaller. Therefore, the decomposition residue can be easily evaporated and removed by heat treatment.

In a case of using hydrofluoric acid in a liquid state, a hydrofluoric acid aqueous solution is usually used. However, the concentration of hydrofluoric acid in this hydrofluoric acid aqueous solution is about 50% or less. Therefore, even if the hydrofluoric acid aqueous solution is vaporized and used for vapor phase decomposition, vapor phase decomposition of the silicon nitride film takes a long time (for example, 10 hours or more) because the concentration of hydrofluoric acid is too low. In this case, not only the time of the entire metal analysis becomes longer, but also the particles of the decomposition residue (for example, ammonium fluorosilicate) become larger. Therefore, it is difficult to remove the decomposition residue by heat treatment.

Further, without the water, wettability of the hydrofluoric acid on the silicon nitride film is poor, and it is difficult for the hydrofluoric acid to come into contact with the silicon nitride film. Therefore, the etching rate of the silicon nitride film by the hydrofluoric acid gas is lowered, and vapor phase decomposition of the silicon nitride film takes a longer time.

Meanwhile, when spraying the water in a liquid state to vaporize the water, the pretreatment device 10 according to the present embodiment mixes the hydrofluoric acid gas with a high concentration into the water and introduces the mixed gas of the vaporized water and the hydrofluoric acid in a gas state into the chamber 100. This can shorten the time of vapor phase decomposition of the silicon nitride film, so that the time of metal analysis of the silicon nitride film or the silicon oxynitride film can be shortened. Furthermore, the particles of the decomposition residue can be made smaller. Therefore, the decomposition residue can be easily removed.

Figure 8:
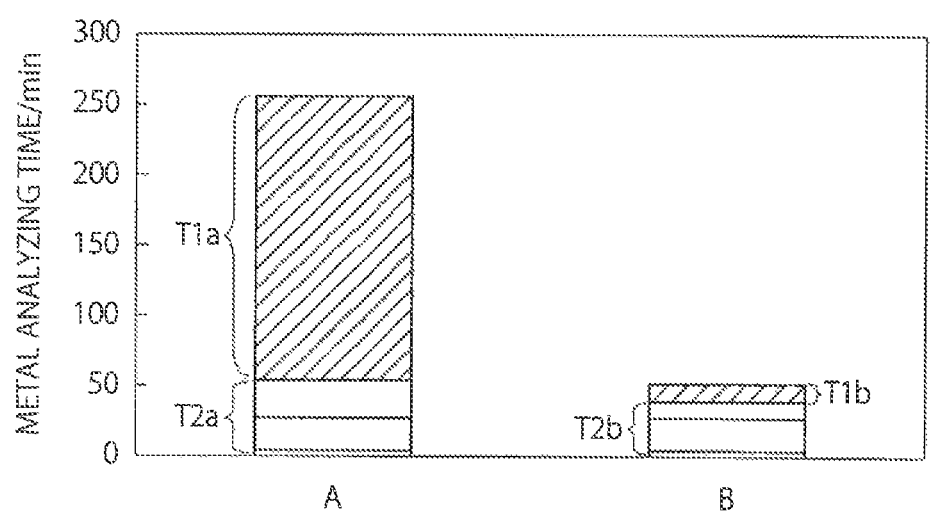
FIG. 8 is a graph showing a time of metal analysis.

FIG. 8 is a graph showing a time of metal analysis. The vertical axis represents a time. The film thickness of a silicon nitride film subjected to vapor phase decomposition is assumed to be about 200 nm.

In FIG. 8, the bar A represents a time of metal analysis in a case where a hydrofluoric acid solution is sprayed by the introducing part 140 with nitrogen gas used as a carrier gas. A flow rate of the nitrogen gas is about 1 l/min. The concentration of hydrofluoric acid in the hydrofluoric acid solution is about 50%. A flow rate (a sprayed amount) of the hydrofluoric acid solution is about 1200 μl/min.

The bar B represents a time of metal analysis in a case where water is sprayed by the Introducing part 140 with hydrofluoric acid gas with a high concentration used as a carrier gas according to the present embodiment. For example, a flow rate of the hydrofluoric acid is about 1 l/min. A flow rate (a sprayed amount) of the water in a liquid form is about 20 μl/min.

Times T1$a$ and T1$b$ in the bars A and B respectively represent times of vapor phase decomposition of the silicon nitride film. Times T2$a$ and T2$b$ respectively represent process times after vapor phase decomposition (times for removing residues, times of metal collection, and times of metal analysis).

As the bars A and B are compared, the difference between the process times T2$a$ and T2$b$ after vapor phase decomposition is relatively small. However, the difference between the vapor phase decomposition times T1$a$ and T1$b$ is very large. That is, the vapor phase decomposition time T1$a$ is extremely long as compared with the vapor phase decomposition time T1$b$.

In a case of using hydrofluoric acid in a liquid state, vapor phase decomposition of a silicon nitride film takes a long time, as described above, because the concentration of the hydrofluoric acid is too low. Further, in a case of not using water, an etching rate of the silicon nitride film by a hydrofluoric acid gas is lowered and vapor phase decomposition of the silicon nitride film takes a long time. In this manner, the vapor phase decomposition time T1$a$ in the bar A becomes very long.

On the other hand, according to the present embodiment, when water in a liquid state is sprayed to be vaporized, a hydrofluoric acid gas with a high concentration is mixed as a carrier gas into the water, and a mixed gas of the vaporized water and the hydrofluoric acid in a gas state is introduced into the chamber 100. Thus, the time of vapor phase decomposition of a silicon nitride film can be shortened. According to the present embodiment, the vapor phase decomposition time T1$b$ of the silicon nitride film is short, and therefore the present embodiment can be applied to an automated analyzing apparatus that automatically performs operations from vapor phase decomposition to collection or analysis.

The time of vapor phase decomposition is preset based on statistics or actually measured values, because the time of vapor phase decomposition depends on the film thickness of the silicon nitride film.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An analysis pretreatment device comprising:
   a chamber configured to contain an analysis object therein;
   a pressure reducer reducing pressure connected to inside the chamber;
   an introducing part vaporizing a liquid and introducing the vaporized liquid into the chamber;
   a tank supplying water in a liquid state to the introducing part; and a cylinder supplying hydrofluoric acid in a gas state to the introducing part, wherein
   the introducing part introduces a mixed gas into the chamber, the mixed gas including a vaporized water, which is obtained by vaporizing water in a liquid state, and hydrofluoric acid in a gas state, wherein the introducing part includes;
   a sprayer;
   the sprayer including:
   a liquid-supply opening receiving water in a liquid state from the tank; a gas-supply opening receiving a hydrofluoric acid gas in a gas state from the cylinder;
   a spray opening mixing the hydrofluoric acid in a gas state into the water, when spraying the water in a liquid form to vaporize the water.

2. The device of claim 1, wherein the analysis object is a nitride film or an oxynitride film provided on a substrate.

3. The device of claim 1, further comprising a collector supplying a chemical liquid onto the substrate after vapor phase decomposition of the analysis object on the substrate, and collecting an object to be measured that remains on the substrate into the chemical liquid.

4. The device of claim 2, further comprising a collector supplying a chemical liquid onto the substrate after vapor phase decomposition of the analysis object on the substrate, and collecting an object to be measured that remains on the substrate into the chemical liquid.

5. The device of claim 1, wherein the cylinder contains hydrofluoric acid with a concentration of 99% or more.

6. The device of claim 2, wherein the cylinder contains hydrofluoric acid with a concentration of 99% or more.

7. The device of claim 3, wherein the cylinder contains hydrofluoric acid with a concentration of 99% or more.

8. The device of claim 1, wherein the introducing part includes a gas-liquid separator separating vaporized water and hydrofluoric acid in a gas state from water in a liquid state.

9. The device of claim 2, wherein the introducing part includes a gas-liquid separator separating vaporized water and hydrofluoric acid in a gas state from water in a liquid state.

10. The device of claim 3, wherein the introducing part includes a gas-liquid separator separating vaporized water and hydrofluoric acid in a gas state from water in a liquid state.

11. The device of claim 1, wherein the cylinder contains a hydrofluoric acid gas therein.

12. The device of claim 2, wherein the cylinder contains a hydrofluoric acid gas therein.

13. The device of claim 3, wherein the cylinder contains a hydrofluoric acid gas therein.

* * * * *